United States Patent [19]

Hoover et al.

[11] Patent Number: 5,464,631
[45] Date of Patent: Nov. 7, 1995

US005464631A

[54] ENCAPSULATED DOSAGE FORMS

[75] Inventors: Charles E. Hoover, Sparta, N.J.; Randy J. Dennin, Greenwood, S.C.; E. Allan Gabor, Summit, N.J.; Mark Schobel, Flemington, N.J.; Albert F. Sorg, Columbia, N.J.

[73] Assignee: Warner-Lambert Company, Morris Plains, N.J.

[21] Appl. No.: 89,925

[22] Filed: Jul. 12, 1993

Related U.S. Application Data

[63] Continuation-in-part of Ser. No. 544,307, Jun. 27, 1990.

[51] Int. Cl.⁶ .................. A61K 9/28; A61K 9/48
[52] U.S. Cl. .................. 424/454; 424/451; 424/546; 424/474; 424/463
[58] Field of Search .................. 424/438, 451, 424/453, 454, 463, 474

[56] References Cited

U.S. PATENT DOCUMENTS

| | | | |
|---|---|---|---|
| 599,865 | 3/1898 | Richards | 427/3 |
| 3,071,513 | 1/1983 | De Bler et al. | 167/83 |
| 4,756,902 | 7/1988 | Harvey et al. | 424/454 |
| 4,820,524 | 4/1989 | Berta | 424/474 |
| 4,867,983 | 9/1989 | Berta | 424/451 |
| 4,921,108 | 5/1990 | Berta | 209/625 |
| 4,928,840 | 5/1990 | Barshay et al. | 220/8 |
| 4,936,074 | 6/1990 | Graham | 53/440 |
| 4,965,089 | 1/1990 | Sauter et al. | 427/3 |
| 4,966,771 | 10/1990 | Berta | 424/478 |
| 4,990,358 | 2/1991 | Berta | 427/3 |
| 5,089,270 | 2/1992 | Hampton et al. | 424/465 |

FOREIGN PATENT DOCUMENTS 0448231  9/1991  European Pat. Off. .

OTHER PUBLICATIONS

Handbook of Chemistry and Physics, Weast, Robert C., CRC Press, Jan. 1977 p. E–45.

*Primary Examiner*—Thurman K. Page
*Assistant Examiner*—James M. Spear
*Attorney, Agent, or Firm*—Charles W. Almer, III

[57]  ABSTRACT

A two color, partially encapsulated medicament that is both tamper resistant and tamper evident comprises at least one pharmaceutically active ingredient, suitable carrier materials and excipients that are compressed into an ovoid, generally cylindrical caplet that is partially encapsulated by its insertion into the body or cap portion of a gelatin capsule.

22 Claims, No Drawings

ENCAPSULATED DOSAGE FORMS

CROSS REFERENCE TO RELATED APPLICATIONS

The present application is a continuation-in-part of U.S. Ser. No. 07/544,307 filed Jun. 27, 1990.

FIELD OF THE INVENTION

The present invention is related to coated or encapsulated pharmaceuticals that can be administered in a caplet-type dosage form. A novel method for preparing gelatin coated pharmaceuticals and the caplets prepared thereby offers tamper evident and tamper-resistance protection as well as greater ease in swallowing so as to encourage better patient compliance.

BACKGROUND OF THE INVENTION

The use of hard gelatin capsules for the containment of pharmaceuticals in unit dosage forms has been known for years. As opposed to tablets wherein the medicament is itself compressed into an ovoid or elliptical cylinder and swallowed directly, gelatin capsules have been used to administer pharmaceuticals in many different forms such as powders, liquids, oils and the like. As opposed to tablets, capsules completely envelop the drug until it reaches the stomach wherein the gelatin coating is eventually dissolved, thereby releasing the medicament for absorption into the bloodstream. This provides an additional benefit of not only taste-masking many otherwise bitter tasting or unpalatable pharmaceuticals and active agents but also provides a lubricous mouthfeel or texture to the surface of the medicament for easier swallowing and passage into the digestive system.

Standard capsules known in the art are prepared by dipping rows of stainless steel pins into solutions of gelatin, starch gelatin or gelatin glycerin. The pins are removed from solution, the dipped portion dried and stripped off the pin. Both capsule halves are formed in this manner. One-half or first portion is generally referred to as the capsule "body" while the half that fits over the open end of the first portion is referred to as the "cap". The cap is mated with the body by fitting its open end over the respective open end of the body. The capsules are generally sold in this assembled manner and the drug or medicament filled later. Commercially available capsule making machines are manufactured by Cherry-Burrell, Cedar Rapids, Iowa 52406 for example.

One of the concerns in the use of hard gelatin capsules in the over-the-counter (OTC) market became evident several years ago when several people died taking a well known analgesic that had been laced with cyanide through tampering. The problem that exists in standard capsule technology of the art is that the two halves of a gelatin capsule can be easily pulled apart and the medicament exposed. Anything can be added or detracted from the composition at this point and the halves then compressed together to again form one whole capsule. Moreover, there is generally nothing that would indicate that the composition inside the gelatin capsule had been changed so as to serve as a warning to any unsuspecting patient or consumer, i.e. there is no tamper-evident indication incorporated into most commercially available gelatin capsules.

The cyanide tampering incidents forced many if not all prescription and over-the-counter pharmaceutical manufacturers to take additional packaging steps to insure that such tampering could not occur without it at least being noticed by the otherwise unsuspecting patient prior to a possibly fatal consumption. "Blister packs", safety sealed bottles and other forms of safety packaging rapidly appeared throughout the pharmaceutical industry in an effort to prevent any further tampering. Some capsule products were withdrawn from the OTC market altogether and in some cases were replaced by "caplets", solid oblong tablets comprised of the medicament and coated with a material such as cellulose, pectin, synthetic polymers and the like. The solid caplet form of the drug not only protected against further tampering since the caplet would have to be broken apart in order to incorporate any additional ingredients and this lack of caplet integrity is easily discernible, but the coating also provides a certain amount of ease in swallowing and protects some medicaments such as aspirin from causing stomach distress.

However, all of these reactionary measures and their precautions have added additional expense to the manufacture and packaging of OTC drugs. U.S. Pat. Nos. 4,820,524; 4,990,358 and 4,921,108 to Berta also points out that beyond the additional cost factors of these precautions, consumer surveys suggest that the shiny, familiar capsule shape has a special appeal to patients as being easy to swallow. It is additionally theorized that consumers perceive capsuled medicaments as being more effective in light of the long term association of the capsule with many well known and well respected pharmaceutical companies and their products. This could possibly add an additional placebo factor to their actual effectiveness. There exists then, a very real need for truly tamper-resistant capsule or capsule-like encapsulating materials as carriers for pharmaceuticals and other OTC medicaments.

Consumer surveys and studies have also shown that as a definite outgrowth of the capsule preference mentality, there is also a strong preference for bi-colored or two-tone colored capsules. These two color capsule dosage forms are preferred since they quickly and readily assure the consumer that they are getting an encapsulated medication merely by a brief, visual examination.

Secondly, the two colored capsules allow for the development of product recognition as the consumer comes to relate a particular combination of colors with a particular medication and manufacturer and thereby creates brand recognition and loyalty which benefits all involved.

A number of references teach and disclose the preparation of coated pills or tablets by dipping them into gelatin solutions of one type or another. U.S. Pat. No. 599,865 to Richards discloses an apparatus for coating pills with gelatin whereby a bar is coated with an adhesive which holds the pills to be coated in place. The bar is then fitted over a second plate containing holes to which the affixed pills are aligned. The bar and plate, once joined, immerse half of the pill body into the gelatin. The bar and plate are then inverted whereby the other half is coated. Whereas the process may coat the pills with a material such as cellulose, starch, etc., the process must be carried out manually and in no way could meet the production demands of today's world.

Of particular interest is U.S. Pat. No. 4,820,520 to Berta wherein a solid medicament core such as a caplet is provided with a capsule-like coating by dipping first one end of the capsule into a gelatinous solution so as to cover one-half of the caplet. This is dried and the other end is then dipped into the solution so that both gelatinous "dips" over-lap at approximately the midway point of the longitudinal axis of the caplet. This over-lapping of the gelatin coats is perceived as the seam created when two solid gelatin capsule halves are joined in the traditional procedure known in the art. U.S. Pat. No. 4,867,983 also to Berta discloses a method whereby the caplet is coated with a first gelatinous core at one end followed by the coating of a second gelatinous core on the other end which is thicker than the first so as to simulate the interlocking halves of a hollow gelatin capsule. The dipping procedure however, must be precise and requires intricate processing and mechanical steps in order to guarantee a smooth gel coating about the caplet. Since two dipping steps are required, the likelihood of uneven coating about the caplet remains high and many caplets are not assured of consistency in capsule shape and size.

Finally, U.S. Pat. No. 5,089,270 to Hampton et. al. discloses a multi-characteristic, bi-layer capsule-shaped tablet consisting of a blend of one or more active ingredients, and may include a first and second coloring agent all of which are longitudinally compressed into a two color capsule. This is then coated but not encapsulated with a hard gelatin shell.

It is an object of the present invention to provide a tamper-resistant and tamper-evident pharmaceutical capsule whereby a medicament in the form of a caplet, is partially encapsulated with one-half of an empty gelatin capsule which is essentially tasteless and easy to swallow.

It is a further object of the present invention to provide a method for partially encapsulating a medicament in the form of a caplet with an empty gelatin capsule by inserting said caplet within one half of said capsule and adhering said caplet thereto.

It is yet a further object of the present invention to provide a capsule-like medicament wherein a solid gelatin capsule body is adhered to the caplet and cannot be removed without substantial damage thereto.

It is yet a further object of the present invention to provide a distinctly bi-colored capsule-like medicament comprised of a solid medicament in the form of a caplet of one color partially encapsulated by the body or cap portion of a gelatin capsule of another color while at the same time allowing for the visual aesthetics of an embossed or debossed design therein.

SUMMARY OF THE INVENTION

The present invention presents a novel method for the partial encapsulation of a solid pharmaceutical or OTC drug in the body portion of a solid gelatin capsule so as to provide a dosage form that is both tamper-resistant and tamper-evident and has the additional advantages of ease in swallowing, taste masking and aesthetic desirability. The partial encapsulation of the caplet by the body portion of the gelatin capsule covers approximately one-half of the caplet and by using two distinctly different colors for each of the caplet and capsule, a two colored dosage form is provided that is readily recognizable and consumer preferred. The inner surface of the capsule body bonds to the surface of the caplet and adheres thereto thereby providing a two colored appearance without having to resort to the more expensive capsule/caplet methodologies known in the art.

DETAILED DESCRIPTION OF THE INVENTION

The present invention deals with the insertion of the body or cap portion of solid, hard gelatin, starch, starch gelatin or gelatin glycerin capsules over and about a solid caplet comprising a pharmaceutical or over-the-counter drug so as to provide several advantages over the uncoated caplets known in the art. For one, the gelatin capsules are tasteless so that by inserting these capsules about a caplet containing an otherwise bad tasting drug, the patient's taste buds are substantially insulated from the bad taste of the drug as it passes through the oral cavity. The capsule does not dissolve or disintegrate until it reaches the stomach and is well past the organoleptic sensory system. Secondly, the caplet/capsule dosage form provides a tamper-resistant and tamper evident feature to any drug so coated since any attempt to incorporate a foreign substance into either portion of the caplet/capsule dosage form of the present invention can only damage the integrity of the medication which is readily noticed. The pharmaceuticals and drugs delivered by the present invention are slowly dissolved in the stomach due to the partial envelopment by the gelatin capsule body and this reduces the likelihood of stomach distress associated with many of the analgesics such as aspirin.

Moreover, the shiny two color aesthetic features of the capsule-shaped medicament have been long associated with well known and trusted products of the pharmaceutical industry and it is believed that this association acts as additional psychological placebo factor in the drugs' actual effectiveness i.e., thereby encouraging better patient compliance. The consumer will perceive this dosage form as a solid two colored capsule with distinct demarcation between the two differently colored halves. And finally, along these lines, the capsules inherently possess a certain ease in swallowing due to the lubricous nature of the gelatin coat and this can only serve to further encourage patient compliance.

The advantage of all of this is that the partially encapsulated, two-color caplet will be a solid dosage form that is tamper-resistant and tamper evident yet possesses the physical characteristics of a gelatin capsule that allow for easier swallowing, the taste masking of bitter drugs and, depending on the capsule, caplet and excipients used, sustained release capabilities. The two-color appearance of the dosage form allows for brand recognition and quite simply provides an aesthetic appearance for the dosage system that is preferred by a vast majority of consumers and patients. Insertion of the caplet within one-half of a gelatin capsule also allows for the visual perception of embossed or debossed letters, logos, symbols and the like that may be placed upon the surface of the caplet. Whereas some of these advantages may be found in the "Gelcap" technology of McNeil Labs (U.S. Pat. Nos. 4,867,983 and 4,921,108 among others), the "Gelcap" approach is complicated and therefore expensive as gelatin dipping techniques are often problematic. The insertion of a caplet into a capsule is simple, fast and efficient and does not require elaborate capsule filling machines for their manufacture.

The core material can be comprised of any prescription pharmaceutical, over-the-counter drug, flavoring agent or sweetener so long as it can be compressed into a solid, oblong cylindrical form known in the industry as a caplet. Suitable medicaments may be selected from the group consisting of any suitable prescription or OTC drug such as antihypertensives, analgesics, antibiotics, anti-tussives, antiarrythmics, antihistamines, antacids, decongestants, laxatives, vitamins, mineral supplements and mixtures thereof. Whereas prescription pharmaceuticals and over-the-counter drugs comprise the preferred embodiments of the present invention, solid forms of sweeteners or flavoring agents may be so encapsulated so as to improve their stability or delay their release rates in certain environments.

In co-pending application U.S. Ser. No. 07/544,307 filed on Jun. 27, 1990 it was discovered that both the cap and body of a gelatin capsule could be "shrink-wrapped" about an entire caplet. A gelatin cap and body with specified water content are placed over a caplet and shrunk thereon using elevated temperature and humidity. A problem encountered however, is that the edges of the cap portion, which generally overlap a portion of the body thereby forming a collar about the mid-point of the longitudinal axis of the caplet, do not always stick to the body but sometimes flange outward from the capsule after shrinkage. Generally, bonding of the capsule cap with the caplet has occurred but the flange is both unsightly and will interfere with proper swallowing of the medicament.

For purposes of this invention, the term "hard gelatin" capsule is meant to include any conventional hard capsule comprised of gelatin, starch, sugar gelatin, gelatin glycerin and mixtures thereof.

Generally, the body portion of the capsule and the caplet are different colors, so as to give the appearance of a bi-colored capsule. Capsule size can be varied according to the dosage of the caplet to be coated.

The body portion of the hard gelatin capsules, once selected according to the size of the caplet to be coated, can be placed about one of the ends of the caplet core either manually or mechanically by making minor modifications to any one of a number of commercially available machines known in the art such as capsule filling machines known as Type 8 and Ultra 8, Capsugel, Greenwood, S.C., and other similar machines manufactured by the Robert Bosch Corp., South Plainfield, N.J., Zanasi Ima Group, Bologna, Italy, and any other suitable hard capsule manufacturing machine such as those made by Capsugel, Greenwood, S.C., Cherry-Burrell, Cedar Rapids, Iowa and Shionogi, Quail-Caps, Inc., Indianapolis, Ind.

The caplet is first formed by mixing at least one selected pharmaceutical active with pharmaceutically acceptable carrier materials and excipients depending upon the drug regimen involved. For example, sustained release of the active may require the incorporation of particular carrier materials that delay its solubility and release to the system while other materials will be required in instances where immediate, up-front solubility and release is required. These materials are well known in the art and may be selected according to the actives involved and the therapeutic effect desired.

Other excipients such as binding agents, anticaking agents, coloring agents, humectants, lubricants and the like are added according to the drug therapy prescribed. In particular with respect to the present invention, a coloring agent is added to produce a color, white included, within the dosage form. Suitable coloring agents are dyes such as D&C Yellow Aluminum Lake #10, D&C Red Aluminum Lake #20, F, D&C Red Aluminum Lake #40 and the like, all of which are well known in the art.

The pharmaceutical active, carrier materials and excipients are compressed into a generally ovoid, cylindrically shaped caplet of a desired size and inserted into the body of the gelatin capsule at one of its ends. The sizes selected should be such that the gelatin capsule covers or encapsulates approximately one half of the caplet body. In one embodiment, the caplet may be adhesively bonded to the gelatin capsule using a pharmaceutically acceptable adhesive solution or film forming agent selected from the group consisting of methacrylic acids, polymers, cellulose and starch derivatives, phthalate derivatives and mixtures thereof. Suitable cellulose derivatives include but are not limited to ethyl cellulose, methyl cellulose, methyl hydroxy cellulose, hydroxypropyl cellulose, hydroxypropyl methyl cellulose, sodium carboxymethyl cellulose and the like. Other suitable film forming agents include polyvinyl pyrrolidone, polyethylene glycol, shellac, cellulose acetate phthalate, polyvinyl acetate phthalate and mixtures thereof.

The adhesive or film forming solution is made up at a concentration ranging from about 1.0% to about 40%, preferably from about 10% to about 25%. The solution, which may be clear, colored, translucent or otherwise, may either be applied to the surface of the caplet prior to insertion or maybe wetted about the inner walls of the gelatin capsule body prior to insertion. The caplet may also be first inserted into the capsule and the solution applied between the surfaces via capillary action. The caplet may also be press-fitted within the body of the capsule using the capsule filling machines and capsule manufacturing machines known in the art and listed, supra. Press fitting, as is known in the art, is the forceful insertion of the caplet into the gelatin cap or body. Over time during storage the high moisture containing gelatin capsules lose water and shrink to a minor extent about the caplet core, thereby adhering to them.

The gelatin capsule will also be colored with a pharmaceutically acceptable coloring or dye so that it has a color different from that of the caplet and thereby exhibits a two-color appearance for the medicament dosage form when the caplet is firmly ensconced in the gelatin capsule. Optionally, an additional coating may be applied to the surface of the encapsulated caplet to further simulate the appearance and function of a gelatin capsule. These coating solutions may be selected from any one of many known in the art but are preferably that of gelatin or a film-forming polymeric substance. Suitable coating materials may, for example, be selected from the group consisting of methylcellulose, hydroxypropyl methyl cellulose, polyvinyl pyrrolidone, ethyl cellulose, various derivatives of methacrylic acids and methacrylic acid esters, cellulose acetate phthalate and the mixtures thereof. These are also applied in solutions with a concentration of from about 10% to about 40%.

Whereas it is recognized that numerous variations and alternative compositions may be utilized that are not specifically set forth above, they are only minor in nature and should not be considered as falling outside the spirit and scope of the present invention as recited by the following claims.

What I claim is:

1. A tamper resistant and tamper evident medicament dosage form comprising an active pharmaceutical ingredient, pharmaceutically acceptable carrier materials and excipients that are compressed into a generally ovoid, cylindrically shaped medicament caplet that is partially encapsulated by a gelatin capsule, wherein said caplet is of a first color and said gelatin capsule is of a second, different color and wherein said caplet is adhesively bonded to said gelatin capsule.

2. The medicament dosage form of claim 1 wherein said active pharmaceutical is selected from the group consisting of antihypertensives, analgesics, antibiotics, anti-tussives, anti-arrythmics, antihistamines, antacids, decongestants, laxatives, vitamins, mineral supplements and mixtures thereof.

3. A tamper resistant and tamper evident medicament dosage form comprising an active pharmaceutical ingredient, pharmaceutically acceptable carrier materials and excipients that are compressed into a generally ovoid, cylindrically shaped medicament caplet that is partially encapsulated by a gelatin capsule, wherein said caplet is of a first color and said gelatin capsule is of a second, different color and wherein said caplet is press-fitted into said gelatin capsule.

4. The medicament dosage form of claim 3 wherein said active pharmaceutical is selected from the group consisting of antihypertensives, analgesics, antibiotics, anti-tussives, anti-arrythmics, antihistamines, antacids, decongestants, laxatives, vitamins, mineral supplements and mixtures thereof.

5. A method for the production of a two colored tamper resistant and tamper-evident medicament dosage form comprising:
   a) blending at least one suitable pharmaceutically active material with selected carrier and excipient materials,
   b) compressing a suitable dosage amount of said mixture into a generally ovoid, cylindrically shaped caplet, said caplet being of a first color and;
   c) inserting said caplet into the cap or body portion of a gelatin capsule, said gelatin capsule being of a second, different color in a manner such that said caplet is press-fitted within said capsule.

6. The medicament dosage form of claims 1 wherein said caplet is adhesively bonded to said gelatin capsule using an adhesive solution selected from the group consisting of ethyl cellulose, methyl cellulose, methyl hydroxy cellulose, hydroxypropyl cellulose, hydroxypropyl methyl cellulose, sodium carboxymethyl cellulose, polyvinyl pyrrolidone, polyethylene glycol, shellac, cellulose acetate phthalate, polyvinyl acetate phthalate, methacrylic acid polymers and mixtures thereof.

7. The medicament dosage form of claim 6 wherein said solution is of a concentration ranging from about 0.1% to about 40% by weight.

8. The medicament dosage form of claim 7 further comprising an additional coating about the uncoated caplet and capsule portions.

9. The medicament dosage form of claim 8 wherein said coating is applied as a solution selected from the group consisting of gelatin and film forming polymeric substances.

10. The medicament dosage form of claim 9 wherein said additional coating is comprised of a solution consisting of methyl cellulose, hydroxy-propylmethyl cellulose, polyvinylpyrrolidone, ethyl cellulose, methacrylic acid copolymers, cellulose acetate phthalate and mixtures thereof.

11. A method for the production of a two colored tamper resistant and tamper-evident medicament dosage form comprising:
   a) blending at least one suitable pharmaceutically active material with selected carrier and excipient materials,
   b) compressing a suitable dosage amount of said mixture into a generally ovoid, cylindrically shaped caplet, said caplet being of a first color and;
   c) inserting said caplet into the cap or body portion of a gelatin capsule, said gelatin capsule being of a second, different color, in a manner such that said caplet is adhesively bonded to said capsule.

12. The method of claim 11 wherein said pharmaceutically active material is selected from the group consisting of antihypertensives, analgesics, antibiotics, anti-tussives, anti-arrythmics, antihistamines, antacids, decongestants, laxatives, vitamins, mineral supplements and mixtures thereof.

13. The method of claim 11 wherein said adhesive is applied in the form of a solution.

14. The method of claim 13 wherein said adhesive is applied to the surface of the caplet prior to insertion thereof into the gelatin capsule.

15. The method of claim 14 wherein said adhesive is applied to the inside surface of the capsule prior to insertion of the caplet.

16. The method of claim 15 wherein said caplet is first inserted into the body of the gelatin capsule and said solution is applied to the encapsulated portion by means of capillary action.

17. The method of claims 14, 15 or 16 wherein said adhesive solution is selected from the group consisting of ethyl cellulose, methyl cellulose, methyl hydroxy cellulose, hydroxypropyl cellulose, hydroxypropyl methyl cellulose, sodium carboxymethyl cellulose, polyethylene glycol, shellac, cellulose acetate phthalate, polyvinyl acetate phthalate, methacrylic acids and their ester copolymers, polyvinyl pyrrolidone, polyvinyl acetate and mixtures thereof.

18. The method of claim 17 wherein the concentration of said adhesive solution ranges from about 1.0% to about 40.

19. The method of claim 18 wherein a second coating solution is applied to the surface of the partially encapsulated caplet.

20. The method of claim 19 wherein said second coating solution is selected from the group consisting of gelatin, film forming polymeric materials and mixtures thereof.

21. The method of claim 20 wherein said film forming polymeric material is selected from the group consisting of methylcellulose, hydroxypropyl methyl cellulose, polyvinylpyrrolidone, ethyl cellulose, methacrylic acid, and mixtures thereof.

22. The method of claim 5 wherein said active pharmaceutical is selected from the group consisting of antihypertensives, analgesics, antibiotics, anti-tussives, anti-arrythmics, antihistamines, antacids, decongestants, laxatives, vitamins, mineral supplements and mixtures thereof.

\* \* \* \* \*

UNITED STATES PATENT AND TRADEMARK OFFICE
CERTIFICATE OF CORRECTION

PATENT NO.    : 5,464,631
DATED         : November 7, 1995
INVENTOR(S)   : Charles E. Hoover et al.

It is certified that error appears in the above-identified patent and that said Letters Patent is hereby corrected as shown below:

Title page,
Item [75], Inventors, should read -- Jean Claude LeBrun of Colmar, France --

Column 7,
Line 32, please correct "0.1%" to read -- 1.0% --

Signed and Sealed this

Twelfth Day of April, 2005

JON W. DUDAS
*Director of the United States Patent and Trademark Office*